(12) United States Patent
Fan et al.

(10) Patent No.: US 10,433,936 B2
(45) Date of Patent: Oct. 8, 2019

(54) SCAN BODY WITH SNAP-IN RETENTION CAPABILITY

(71) Applicant: EVOLLUTION IP HOLDINGS, INC., Birmingham, AL (US)

(72) Inventors: Haibo Fan, Woodbridge, CT (US); Boris Simmonds, Vestavia, AL (US); Fred J. Molz, IV, Birmingham, AL (US)

(73) Assignee: EVOLLUTION IP HOLDINGS, INC., Birmingham, AL (US)

( * ) Notice: Subject to any disclaimer, the term of this patent is extended or adjusted under 35 U.S.C. 154(b) by 154 days.

(21) Appl. No.: 15/363,183

(22) Filed: Nov. 29, 2016

(65) Prior Publication Data

US 2017/0151038 A1 Jun. 1, 2017

Related U.S. Application Data

(60) Provisional application No. 62/261,613, filed on Dec. 1, 2015.

(51) Int. Cl.
| | |
|---|---|
| *A61C 8/00* | (2006.01) |
| *A61B 6/12* | (2006.01) |
| *A61B 6/14* | (2006.01) |
| *A61C 9/00* | (2006.01) |
| *A61B 90/00* | (2016.01) |

(52) U.S. Cl.
CPC .............. *A61C 8/0001* (2013.01); *A61B 6/12* (2013.01); *A61B 6/14* (2013.01); *A61C 8/006* (2013.01); *A61C 8/0012* (2013.01); *A61C 8/0074* (2013.01); *A61C 9/0053* (2013.01); *A61B 2090/3966* (2016.02); *A61C 2201/002* (2013.01); *A61C 2201/005* (2013.01)

(58) Field of Classification Search
CPC ..... A61C 8/0001; A61C 8/006; A61C 8/0074; A61C 8/0012; A61C 9/0053
See application file for complete search history.

(56) References Cited

U.S. PATENT DOCUMENTS

| | | | | |
|---|---|---|---|---|
| 5,904,483 | A * | 5/1999 | Wade | A61C 8/0048 433/173 |
| 6,508,650 | B2 * | 1/2003 | Gittleman | A61C 8/0001 433/172 |
| 7,163,398 | B2 * | 1/2007 | Klardie | A61C 8/0001 433/173 |

(Continued)

FOREIGN PATENT DOCUMENTS

| | | |
|---|---|---|
| EP | 2462893 B1 | 3/2014 |
| WO | 2016012581 A1 | 1/2016 |

OTHER PUBLICATIONS

Camlog Titanium Bases CAD/CAM; 4 pgs; date unknown.
International Search Report & Written Opinion for PCT/US2019/019990; dated May 14, 2019; 11 pgs.

*Primary Examiner* — Ralph A Lewis
(74) *Attorney, Agent, or Firm* — Gardner Groff & Greenwald, PC (57) ABSTRACT

A scan body for intraoral scanning includes a snap-in retention capability for engagement with a dental implant having a first engagement section. The second engagement section is configured for a snap-in or frictional fit with the first engagement section to releasably secure the scan body to the implant.

33 Claims, 4 Drawing Sheets

(56) References Cited

U.S. PATENT DOCUMENTS

| | | | |
|---|---|---|---|
| 7,654,824 B2 * | 2/2010 | Ebi | A61C 8/0001 433/173 |
| 8,002,547 B2 * | 8/2011 | Porter | A61C 8/0001 433/173 |
| 9,357,927 B2 | 6/2016 | Thomsen | |
| 2007/0281278 A1 * | 12/2007 | Jorneus | A61C 8/0001 433/173 |
| 2008/0176188 A1 * | 7/2008 | Holzner | A61C 8/0001 433/215 |
| 2008/0206709 A1 | 8/2008 | Lannan | |
| 2012/0214130 A1 * | 8/2012 | Krivoruk | A61C 8/0048 433/173 |
| 2013/0196290 A1 * | 8/2013 | Herrington | A61C 8/006 433/173 |

\* cited by examiner fig.3 fig.4

SCAN BODY WITH SNAP-IN RETENTION CAPABILITY

CROSS-REFERENCE TO RELATED APPLICATION

This application claims the benefit of U.S. Provisional Patent Application Ser. No. 62/261,613 filed Dec. 1, 2015, the entirety of which is hereby incorporated by reference herein.

TECHNICAL FIELD

The present invention relates generally to the field of dental implants and prosthetics, and more particularly to a scan body having snap-in retention capability for use with a dental implant or implant analog.

BACKGROUND

Scan bodies are typically used in the dental industry once an implant has been set within a patient's jaw such that a digital restorative pathway (via intraoral scanning) can be created to determine the size, shape and orientation of a final restoration or prosthesis to be fitted on the implant. In most cases, scan bodies are generally fastened to the implant with an abutment screw, which generally requires a clinician to manually screw the abutment screw to the implant. One drawback to manually screwing an abutment screw within the implant to fasten the scan body to the implant is that some installation drivers can be long, requiring a significant amount of vertical space, thereby making placement of the abutment screw difficult in the posterior of a patient's mouth where vertical space is often limited. Another drawback is due to the time required to manually place and remove the abutment screw to/from the implant before and after scanning the scan body. And the abutment screw can be dropped in the patient's mouth before placement or after removal, which may present an aspiration risk.

Accordingly, it can be seen that needs exist for an improved scan body for use with dental implant procedures. It is to the provision of an improved scan body meeting these and other needs that the present invention is primarily directed.

SUMMARY

In example embodiments, the present invention provides a scan body having snap-in retention capability for engagement with a dental implant or an implant analog. The scan body is capable of snapping in or frictionally engaging the implant or implant analog such that no fasteners or screws are required to retain the scan body temporarily in place on the implant or implant analog.

In one aspect, the invention relates to a scan body for snap-in retention with a dental implant. The implant includes a first engagement section. The scan body includes an elongate body extending from a first end to a second end. The elongate body includes a first end portion including a scan feature, an upper section positioned adjacent the first end portion and having a generally uniform cylindrical portion including a channel extending at least partially through the cylindrical portion, a lower section positioned adjacent the upper section, a second engagement section positioned adjacent the lower section and having at least one engagement rib, and an end post for axial alignment within an internal threaded portion of the implant.

In example embodiments, the second engagement section includes a male hex (i.e., hexagonal) profile, the first engagement section includes a female hex profile, and the male and female hex profiles are configured for cooperative interengagement therebetween.

In example embodiments, the at least one engagement rib of the male hex profile is sized at least slightly larger than the size of the female hex profile such that the male hex is provided with a snap-in frictional fit with the female hex. In example embodiments, the male hex includes at least one engagement rib on at least three of its six surfaces. In example embodiments, a sleeve is provided for fitting on the lower section of the elongate body. In example embodiments, the sleeve is formed from a titanium alloy or other radiopaque material. In example embodiments, the sleeve allows for proper seating verification of the scan body within the implant via x-ray imaging. In example embodiments, the elongate body is formed from polyether ether ketone plastic.

In example embodiments, the scan feature of the first end portion includes one or more flats, wherein the flats are configured to be recognized by an intraoral or table top scanner. In example embodiments, the scan feature includes three flats, wherein two of the three flats are oriented generally parallel to each other, and wherein one of the three flats is oriented generally perpendicular relative to the other two flats. In example embodiments, the sleeve is color coded by anodizing to match a platform color of the implant. In example embodiments, the second engagement section of the scan body is configured for engagement with both a dental implant and/or with an implant analog.

In another aspect, the invention relates to a snap-in scan body for removable engagement with an implant, the implant including a first engagement section. In example embodiments, the snap-in scan body includes an elongate body extending from a first end to a second end, a first end portion positioned at the first end and having a scan feature including one or more flats, an upper section positioned adjacent the first end portion and including a cylindrical channel formed therein and a lower rib, a lower section positioned adjacent the upper section and having a central rib and a lower rib, a second engagement section positioned adjacent the lower section and having at least one engagement rib for frictionally engaging the first engagement section, and an end post positioned adjacent the second engagement section at the second end of the snap-in scan body.

In example embodiments, the first engagement section includes a female hex, the second engagement section includes a male hex, and the male and female hex are configured for interengagement therebetween. In example embodiments, at least one engagement rib is provided on a surface of the male hex. In example embodiments, the male hex includes at least one engagement rib on at least three surfaces.

In example embodiments, the snap-in scan body further includes a sleeve for fitting on the lower section of the elongate body, wherein the sleeve allows for proper seating verification of the male hex of the second engagement section of the scan body within the female hex of the first engagement section of the implant via x-ray. In example embodiments, the sleeve is formed from a titanium alloy or other radiopaque material. In example embodiments, the elongate body is formed from polyether ether ketone plastic. In example embodiments, the sleeve is color coded by anodizing to match a platform color of the implant. In example embodiments, the second engagement section of the scan body is configured for removable engagement with both an implant and with an implant analog.

In still another aspect, the invention relates to a method of fastening a scan body to an implant. The method includes providing an implant, the implant having a first engagement section; providing a scan body, the scan body having a second engagement section, the second engagement section being generally complementary in shape to the first engagement section; providing at least one engagement feature on at least a portion of the second engagement section, the at least one engagement feature generally protruding outwardly from the second engagement section; engaging the second engagement section of the scan body with the first engagement section of the implant such that the at least one engagement feature of the second engagement section frictionally engages at least a portion of the first engagement section. In example embodiments, the at least one engagement feature of the second engagement section is in the form of a rib.

In yet another aspect, the invention relates to a scan body for snap-in retention with a dental implant or implant analog. The implant or implant analog includes a first engagement section. The scan body includes an elongate body extending from a first end to a second end. The elongate body includes a first end portion, an upper section, a lower section, a second engagement section having at least one engagement rib, and an end post. In example embodiments, the scan body is used with an implant when using an intra oral scanner, and wherein the scan body is used with an implant analog when using a table top scanner.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of example embodiments of the invention, and are not restrictive of the invention, as claimed.

DETAILED DESCRIPTION OF EXAMPLE EMBODIMENTS

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
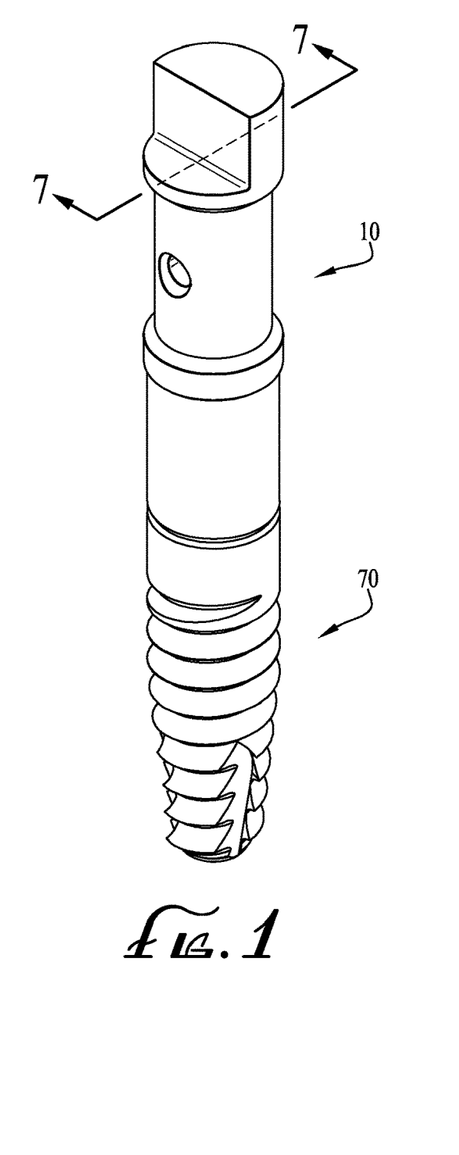
FIG. 1 is a perspective view of a scan body assembled with a dental implant according to an example embodiment of the present invention.
Figure 2:
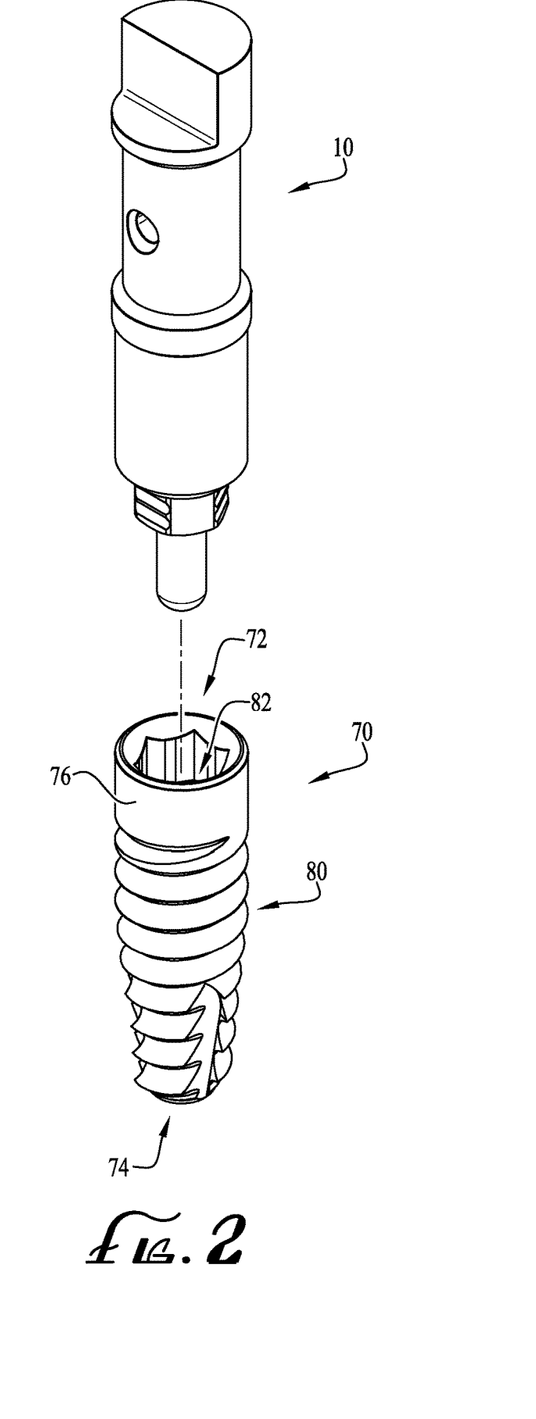
FIG. 2 is an assembly view of the scan body and implant of FIG. 1.

With reference now to the drawing figures, wherein like reference numbers represent corresponding parts throughout the several views, FIGS. 1-2 show a scan body assembly 10 for use with a dental implant 70 according to an example embodiment of the present invention. In example embodiments, the scan body assembly 10 enables a dental clinician to scan a patient's mouth with dental imaging equipment (e.g., intraoral scanner) to provide a digital dental restorative pathway, for example, so that a prosthesis can be fabricated to engage with the implant 70 that is engaged with the patient's jaw. Preferably, the scan body assembly 10 is configured such that no separate fasteners, screws, etc. are required for mounting the scan body assembly 10 to the implant 70.

In example embodiments, the scan body assembly 10 is used with a dental implant 70, for example when using an intra oral scanner. Thus, with the implant secured within the bone structure of the patient's jaw, the scan body assembly is releasably engaged by a frictional fit or snap coupling with the implant 70, and the intra oral scanning can be performed. According to other example embodiments, the scan body assembly 10 can be used with an implant analog (e.g., model of the patient's dentition formed by an impression), for example, wherein the scan body assembly 10 can be frictionally engaged with the implant analog. As such, the scan body assembly 10 as described herein may be provided for use with an implant when using an intraoral scanner or alternatively may be provided for engagement with an implant analog when using a table top scanner. Accordingly, the scan body assembly 10 provides for dual functionality whereby the scan body assembly 10 can be used with implants (using an intra oral scanner), or whereby the scan body 10 can be used with an implant analog (using a table top scanner). For example, a practicing clinician can use the same scan body assembly 10 for reusable and removable engagement with an implant and an implant analog, or can optionally be configured for a preferred engagement with either of the implant or the implant analog, for example, when the engagement sections of the implant and implant analog are not complementary with each other.

The implant 70 overall is generally cylindrical in shape and extends from a first end 72 to a second end 74. The first end 72 includes a peripheral surface 76 and the second end 74 comprises threads 80. Generally, the threads 80 extend from the second end 74 to a portion of the peripheral surface 76. The first end 72 defines a generally centrally-positioned orifice that comprises an engagement body, socket or other surfaces or features forming a first engagement section 82, such as a female receiver or socket for a hexagonal driver, and an internal threaded portion 84 (see FIGS. 7-8). Preferably, the first engagement section 82 is provided for receiving and releasably engaging a receiver, plug or other surfaces or features forming a second engagement section 54 of the scan body assembly 10 (as will be described below). Optionally, one or more self-tapping flutes can be formed on the implant 20 near the second end 74.

Figure 3:
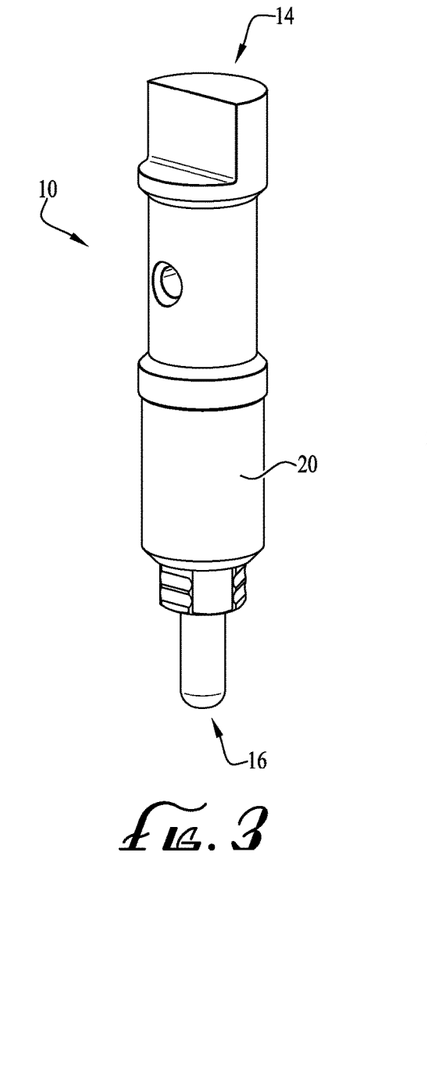
FIG. 3 is a perspective view of the scan body of FIG. 1.
Figure 4:
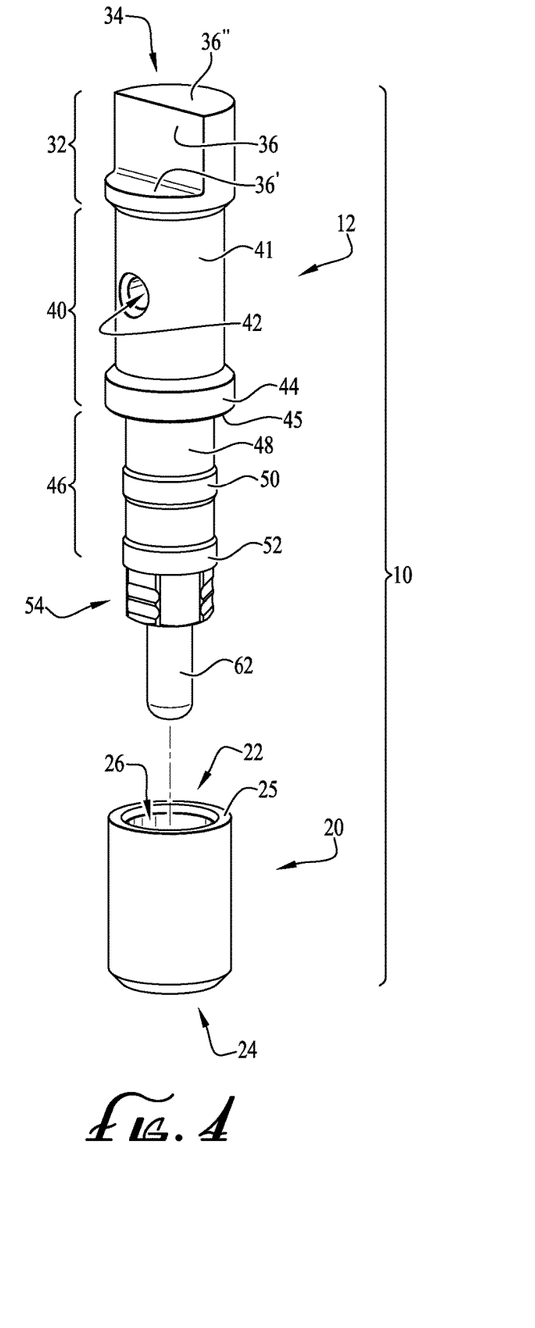
FIG. 4 is an assembly view of the scan body of FIG. 3, showing a sleeve component separated therefrom.

As depicted in FIGS. 3-4, the scan body assembly 10 generally comprises an elongate body 12 and a sleeve 20 configured for engagement onto a portion of the elongate body 12. The elongate body 12 generally comprises a first end 14 and a second end 16 generally opposite thereto. In example embodiments, the elongate body 12 generally comprises a first end section 32, an upper section 40, a lower section 46, the second engagement section 54, and an end post 62 (see FIG. 4). According to one example embodiment, the elongate body 12 is formed from a material suitable for dental applications (e.g., polyether ether ketone plastic (PEEK)), for example, which may be formed by an injection molding and/or milling process. In alternate example embodiments, the elongate body 12 can be formed from a radiopaque plastic (e.g., PEEK with barium sulfate), or can optionally be formed from other plastics or metals. In example embodiments, the elongate body 12 is integrally formed as one unitary piece. Alternatively, one or more portions of the elongate body 12 may be formed separately and connected together. The sleeve 20 is generally formed from a metallic material such as ASTM F-136 titanium alloy. In example embodiments, the sleeve 20 is formed from a metallic material to allow for X-ray seating verification, for example, so that the clinician can ensure that the scan body (and sleeve fitted thereon) is properly seated and fitted within the implant 70 during the scanning procedure. In alternate embodiments, the sleeve 20 can be formed from other materials, for example, a metal such as stainless steel or cobalt-chromium (CoCr), or a radiopaque plastic material.

In example embodiments, the sleeve 20 is optionally provided in one of a plurality of colors (e.g., which are generally anodized) so that the scan body assembly 10 is color coded whereby the clinician can easily identify the assembly 10 and place the assembly 10 in the appropriate implant (e.g., having same color as the sleeve 20). For example, in example embodiments, the implant (or portions thereof) may also be colored to correspond to the scan body assembly 10. Thus, during procedures where more than one scan body assembly is required (e.g., multiple implants each requiring a prosthesis), each of the scan body assemblies will be colored differently to correspond to the correct implant. According to example embodiments, the sleeve 20 can be anodized or otherwise treated or colored to apply a desired color thereto, for example, to match the color of the implant prosthetic platform color.

As depicted in FIG. 4, the first end portion 32 comprises a scan feature 34 including one or more flats 36, 36', 36". In example embodiments, the scan feature 34 comprises three flats 36, 36', 36", for example, whereby two of the flats 36', 36" are generally oriented parallel to each other and the other flat 36 is generally oriented perpendicular relative to the other two flats 36', 36". Preferably, the flats 36, 36', 36" are capable of being scanned and recognized by an intraoral or tabletop scanner, which allows for the creation of a digital restorative pathway (e.g., 3-dimensional model) of the patient's dental area. In example embodiments one or more portions of the scan feature(s) and/or other portions of the scan body assembly comprise an x-ray imagable material or material(s) compatible with alternative clinical imaging systems and procedures, sufficient to specify position and orientation of the scan body in engagement with the implant. For example, one or more of the flats 36, 36', 36" can be formed from a radiopaque material, or for example, can be at least partially dipped or coated in a radiopaque material. In example embodiments, the elongate body 12 is entirely formed from a PEEK material, which is blended with barium sulfate prior to molding the body 12, or for example, wherein barium sulfate is applied to an outer surface of one or more portions of the body 12.

The upper section 40 is generally positioned adjacent to the first end portion 32 and comprises a generally uniform cylindrical portion 41, a cylindrical channel 42 extending through the cylindrical portion 41, and a lower rib 44 extending around the entirety of the periphery of the cylindrical portion 41. In alternate embodiments, the cylindrical channel 42 can be otherwise shaped and configured to extend entirely through the cylindrical portion 41, or for example, may extend through at least a portion of the cylindrical channel 42. In example embodiments, the channel 42 is preferably sized such that a dental tool or probe is capable of being inserted at least partially therein, for example, such that the assembly 10 can be removed from disengagement with the implant 70, for example by retraction using a dental probe or other tool engaged in the channel 42. The lower section 46 is generally adjacent to the upper section 40 and comprises a cylindrical portion 48 and a pair of spaced-apart ribs 50, 52 extending around the entirety of the periphery of the lower section 46. According to example embodiments, the cylindrical portion 48 of the lower section 46 generally comprises a smaller diameter than the cylindrical portion 41 of the upper section 40. Preferably, the lower rib 44 of the upper section is sized to be at least slightly larger than an opening 26 of the sleeve 20, for example, such that the sleeve is not permitted to move beyond the lower rib 44. For example, according to example embodiments, the lower rib 44 comprises an engagement surface or shoulder 45 that is generally configured for direct engagement with an engagement or contact surface 25 of the sleeve 20. Furthermore, the ribs 50, 52 of the lower section 46 are preferably sized to be substantially similar to the size of the opening 26 of the sleeve 20, for example, so that there is at least some amount of friction for retaining the sleeve 20 on the lower section 46, for example having a transition or close sliding fit therebetween. Optionally, the sleeve 20 may be generally movable relative to the ribs 50, 52 without much friction therebetween, for example with a close running fit; optionally including one or more engagement features formed on the sleeve and/or the body 12 to provide for engagement and retention between the sleeve and the lower section 46.

The second engagement section 54 is generally positioned adjacent the lower section 46 and is preferably complementary in shape to the first engagement section 82 of the implant 70. The second engagement section 54 may be a male polygonal body (such as a hexagonal protrusion), and similarly, the first engagement section may be a female polygonal (for example hexagonal) plug, for example, so that the male polygonal body is capable of cooperative engagement with the female polygonal plug. In example embodiments, the configuration of the male body and female plug may be commonly known as external (plug) and internal (socket) rotational hex drive profiles. In other example embodiments, other configurations of engagement sections (including non-polygonal surfaces) may be employed. For example, according to example embodiments, the second engagement section can be configured and adapted for cooperative engagement with other known implant systems (e.g., Nobel Biocare® NobelReplace™, Straumann®, etc.). The profile and configuration of the first and second engagement surfaces preferably retain the scan body in the implant and prevent rotation of the scan body relative to the implant. The profile and configuration of the second engagement section optionally matches or corresponds at least in part to the profile and configuration of a dental implant abutment mount to which a dental prosthesis is mounted for compatibility with the implant. Furthermore, an end post 62 extends from adjacent the second engagement section 54 to the second end 16. According to example embodiments, the end post 62 is configured to maintain axial alignment of the scan body assembly 10 with the implant 70, for example, wherein the end post 62 is generally sized to fit within the internal threaded portion 84 of the implant (see FIGS. 7-8).

Figure 5A:
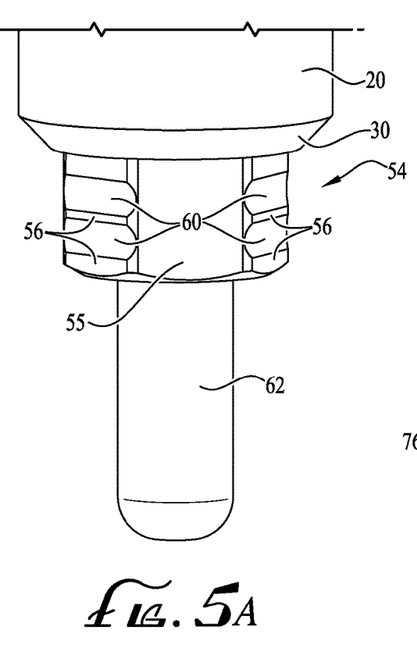
FIG. 5A is a detailed perspective view of a base portion of the scan body of FIG. 3.

As depicted in FIG. 5A, the second engagement section 54 of the scan body preferably comprises one or more surface features formed thereon for frictionally or otherwise releasably and positively engaging the first engagement section 82 of the dental implant 70. For example, in the depicted embodiment at least one of the surfaces of the engagement section 54 comprises one or more snap-in releasable engagement features or engagement ribs 56. In example embodiments, the engagement ribs 56 generally extend horizontally along at least one of the surfaces, and a groove 60 or flat generally extends along one or more sides of the engagement ribs 56. In example embodiments, the engagement ribs 56 are dimensioned to be at least slightly larger than a majority of the surface it is formed on for providing a frictional engagement fit with the first engagement section 82. For example, where the first engagement section 82 is a female hexagonal ("hex") configuration and the second engagement section 54 is a male hex configuration, the engagement ribs 56 extend or project outwardly at least partially beyond the dimension of the female hex of the first engagement section 82, for example, so that there is at least a slight amount of interference between the first and second engagement sections to provide for a releasable or detachable friction fit therebetween.

Figure 5B:
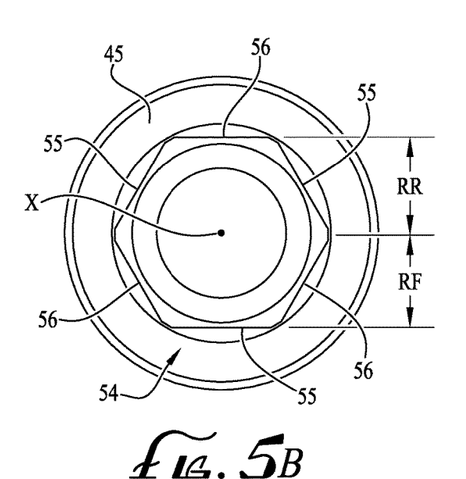
FIG. 5B is an end view of the base portion of the scan body of FIG. 5A.
Figure 6:
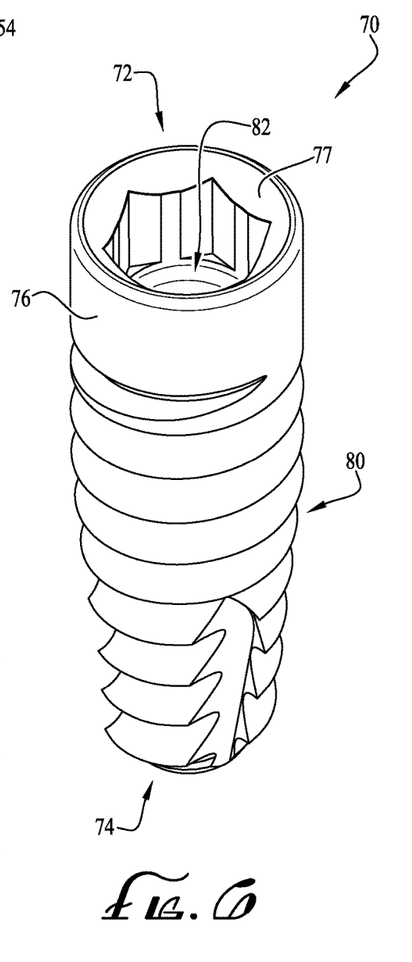
FIG. 6 is a perspective view of the implant of FIG. 2.

According to example embodiments and as depicted in FIG. 5B, at least three of the six transverse side surfaces of the male hex of the second engagement section 54 comprise one or more engagement ribs 56, which generally extend horizontally or transversely relative to the longitudinal axis X of the elongate body 12. The side surfaces that are not provided with one or more engagement ribs 56 define a smooth and planar surface 55. In example embodiments, every other surface of the male hex comprises one or more of the engagement ribs 56, for example, such that the ribs 56 are generally equally spaced apart around the male hex and whereby engagement with the first engagement section 82 causes the scan body assembly 10 to become axially and concentrically aligned with the implant 70. Thus, in example embodiments, three of the surfaces comprise one or more engagement ribs 56, and the other three surfaces can define generally smooth and planar surfaces 55 (see FIGS. 5A-B). According to example embodiments, the surfaces comprising the engagement ribs 56 define a dimension RR between an outer surface of the rib 56 and an axis X extending axially therethrough, and the smooth finished surface 55 has a dimension of RF that is defined between an outer surface of the finished surface 55 and the X axis. In example embodiments, the dimension RR is between about 0.25%-8% greater than the dimension RF, more preferably between about 0.25%-4%, for example, about 2% according to an example embodiment of the present invention. According to one example embodiment, the dimension RR is about 0.0473 inches and the dimension RF is about 0.0482 inches. Optionally, the dimensional differences between dimension RR and RF can be chosen as desired, for example, to provide for a releasable frictional engagement fit. In example embodiments, the frictional engagement provided between the ribs 56 and the implant are such that a force of between about 0.4-8 lbf is required to cause disengagement between the first and second engagement sections. Alternatively, the elements may be configured for engagement and disengagement with less or greater force.

Optionally, the one or more engagement ribs 56 may take other forms (e.g., tabs, clips, indents, detents, etc.) and be positioned as desired on one or more surfaces of the male hex. Optionally, the engagement feature(s) can comprise a compressible, deformable, spring-biased, or otherwise resilient body or member for positively and removably engaging the implant 70. In further example embodiments, the engagement feature(s) comprise one or more snap-fit couplings. In example embodiments, the female hex of the first engagement section 82 is generally standard without any additional surface or engagement features for providing engagement with the engagement ribs 56. Alternatively, one or more surface features may be formed along one or more surfaces of the female hex of the second engagement section 82 to provide additional interengagement with the engagement ribs 56. Further optionally, the one or more engagement ribs 56 may be generally merged together to form a surface (e.g., by removing the groove 60) such that a substantially larger surface area can be provided with an interference fit with the first engagement section 82 of the female hex. Referring back to FIG. 4, according to example embodiments of the present invention, at least one of the flats 36, 36', 36" of the scan feature 34 is oriented to be parallel with one of the surfaces of the engagement section 54. According to one example embodiment, the generally vertical flat 36 of the scan feature 34 is oriented to be parallel with respect to one of the surfaces of the engagement section 54, for example, such that the scan feature 34 can be properly oriented when removably engaged with the first engagement section of the implant or the implant analog.

Figure 7:
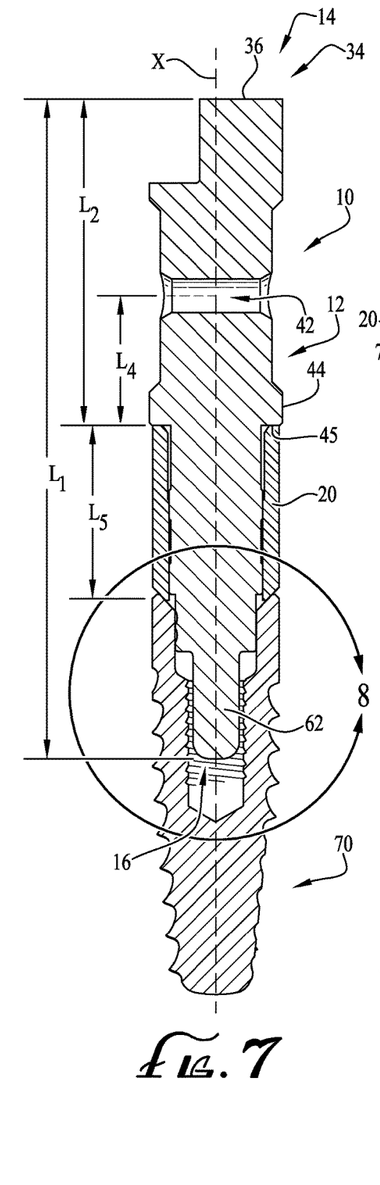
FIG. 7 is a cross-sectional view of the scan body assembled with the implant of FIG. 1 taken along line 7-7, showing a snap-in feature of the scan body removably engaging an engagement feature of the implant.
Figure 8:
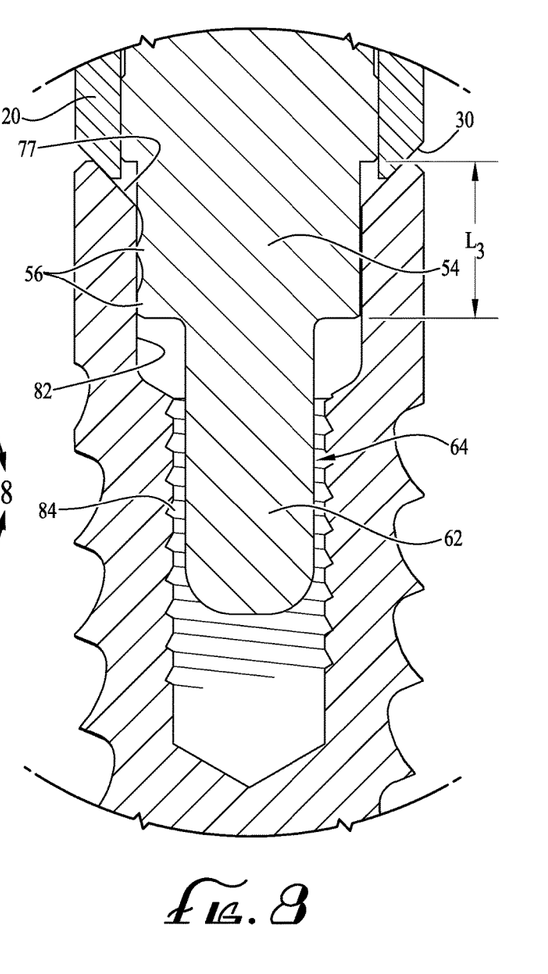
FIG. 8 is a detailed cross-sectional view of FIG. 7 showing the snap-in feature of the scan body removably engaging an engagement feature of the implant.

FIGS. 7-8 show the scan body assembly 10 removably or releasably engaged with the implant 70, for example, wherein the second engagement section 54 is frictionally engaged (e.g., snap-in fit retention) with the first engagement section 82. As shown in FIG. 8, the engagement ribs 56 are frictionally engaged with a surface of the first engagement section 82. Preferably, as mentioned above, the end post 62 (and scan body assembly 10 thereof) is substantially axially aligned with the internal threaded portion 84 of the implant 70 and the sleeve 20 is fully seated with the first end 72 of the implant 70, thereby providing axial alignment along an axis X of the scan body assembly 10 (having a second elongate axis) with the implant 70 (having a first elongate axis). Similarly, when using an analog, the equal distribution of the engagement ribs 56 around the surfaces of the second engagement section 54 preferably provide for axial alignment of the scan body assembly 10 with an elongate axis of the analog. In example embodiments, the post 62 is generally sized and shaped to be at least partially smaller than a diameter defined by the inward-most edge of the internal threaded portion 84, for example, such that an outer periphery portion 64 of the post 62 is generally inwardly offset from the internal threaded portion 84 (see FIG. 8). Preferably, the post 62 provides for precise location during scanning, for example, as the post 62 preferably provides for axially aligning the implant 70 with the scan body assembly. In alternate embodiments, the post 62 can be configured to engage at least a portion of the internal threaded portion 84 during coupling engagement of the first and second engagement sections, which may further provide for assistance in maintaining proper alignment of the scan body assembly with the internal threaded portion of the implant 70.

In example embodiments, a chamfered surface or bevel 30 is formed along an end portion of the sleeve 20 to assist in fully seating with a chamfered surface 77 of the implant 70 when the scan body assembly 10 is fitted within the first engagement section 82 of the implant 70. According to example embodiments, the mating or interface geometry defined between the bevel 30 and the chamfered surface 77 represents a beveled connection. As depicted in FIG. 8, the bevel connection is configured such that about a half of the surface area of the bevel 30 is engaged with about a half of the surface area of the chamfered surface 77. In alternate example embodiments, more or less than about half of the surface areas of the bevel and chamfered surface can be configured to engage when the scan body assembly 10 is fully seated with the implant 70. In example embodiments, with the bevel 30 fully seated and engaged with the chamfered surface 77, x-ray imaging can identify the engagement between the shell and the chamfered surface, for example, to verify that the scan body assembly 10 is fully seated and engaged with the implant, or for example, with an implant analog.

Alternatively, the mating or interface geometry between the sleeve and the implant can be in the form of a square or butt joint (e.g., engagement of flat/parallel surfaces of the sleeve and implant without a bevel or chamfer), or can be configured otherwise such that seating verification is obtainable. For example, the sleeve 20 and/or the second engagement section 54 can be configured and adapted for mating engagement with other known implant systems (e.g., Nobel Biocare® NobelReplace™, Straumann®, Zimmer Biomet or Zimmer dba Zimmer Dental, Biomet 3I, Dentsply, Astra, Implant Direct, CAMLOG®, etc.).

As depicted in FIG. 7, the elongate body 12 extends along a longitudinal axis X and defines a length L1 between the first and second ends 14, 16. In example embodiments, the length L1 is between about 0.25-1.5 inches, more preferably between about 0.5-1 inches, and still more preferably between about 0.75-0.90 inches, for example, between about 0.77-0.80 inches. A length L2 is defined between the first end 14 (or the end surface or flat 36") and the engagement surface 45, a length L3 is defined between an end portion of the rib 52 and an end portion of the second engagement section 54 (see FIG. 8), a length L4 is defined between a central axis of the channel 42 and the engagement section 45 of the rib 44, and the sleeve 20 defines a length L5 extending between the ends thereof (e.g., the upper engagement surface 25 (see FIG. 4) and an end portion of the chamfered surface 30). In example embodiments, the length L2 is generally between about 0.25-0.65 inches, more preferably between about 0.30-0.50 inches, still more preferably between about 0.382-0.388 inches, for example, about 0.385 inches. The length L3 is generally between about 0.038-0.098 inches, more preferably between about 0.048-0.088 inches, still more preferably between about 0.066-0.070 inches, for example, about 0.068 inches. In example embodiments, the length L4 is generally between about 0.133-0.173 inches, more preferably between about 0.143-0.163 inches, for example, about 0.153 inches. And, in example embodiments the length L5 is generally between about 0.157-0.257 inches, more preferably between about 0.182-0.232 inches, still more preferably between about 0.206-0.208 inches, for example, about 0.207 inches. According to example embodiments, the ratio of the lengths L1/L2 is between about 1.5-2.5, more preferably between about 1.75-2.25, for example, about 2. In alternate embodiments, the dimensions and ratios as described herein can be greater or less, to suit the intended application.

In use, the scan body assembly 10 is generally provided for fitting within the patient's mouth in removable engagement within an installed implant before scanning is to begin. In some example embodiments, the clinician places the second engagement section (e.g., male hex) of the scan body assembly within the first engagement section (e.g., female hex) of the implant by grasping the scan body with their fingers or with a tool and firmly seating the first and second engagement sections together. Depending on the tolerance of the fit and/or the interference caused by the engagement ribs of the second engagement section, more or less force may be required to fully seat the second engagement section with the first engagement section. In example embodiments, a light to moderate hand pressure is sufficient. According to example embodiments, one or more X-ray scans or other clinical imaging processes may be performed to verify that the sleeve 20 is seated appropriately with the implant. The clinician then performs the scanning procedure whereby a digital dental restorative pathway of the patient's mouth is created. Once scanning is complete, the clinician then removes the scan body assembly 10 from the implant, for example by grasping the upper section 40 of the elongate body 12 and pulling to overcome the frictional or snap-fit engagement between the at least one engagement rib 56 of the second engagement section 54 with the first engagement section. Optionally, a dental probe or other tool may be utilized to assist in removing the scan body assembly 10 from the implant 70, for example, wherein the tool is inserted into or through the cylindrical channel 42. As described above, in example embodiments, the frictional engagement provided between the ribs 56 and the implant 70 (e.g., first and second engagement sections) is such that a force of between about 0.40-8.01 lbf may be applied to engage and disengage the first and second engagement sections. Alternatively, the components may be configured for a greater or lesser engagement and/or disengagement force.

According to another example aspect, the present invention relates to a method of fastening a scan body to an implant. The method comprises providing an implant, the implant comprising a first engagement section; providing a scan body, the scan body comprising a second engagement section, the second engagement section being generally complementary in shape to the first engagement section; providing at least one rib or other engagement feature or surface on at least a portion of the second engagement section; installing the implant in the mandible or maxilla of a human or animal patient; and engaging the second engagement feature of the scan body with the first engagement feature of the implant such that the second engagement feature positively and releasably engages at least a portion of the first engagement feature. The method then optionally further comprises removing the scan body from the implant.

Thus, according to example embodiments of the present invention, the scan body assembly can be placed and removed from the implant without the need for fasteners such as abutment screws. Placement and removal of the scan body assembly without requiring fasteners saves a substantial amount of time for the clinician, thereby substantially reducing the amount of time a patient must remain in the dental chair. Furthermore, the scan body assembly 10 of the present invention preferably allows for easier placement in the posterior of a patient's mouth where vertical space is often limited. Without the need for a driver or other tool for fastening the abutment screw to the implant, the scan body assembly may be sized to be at least slightly taller than screw-attached scan bodies, with a greater surface area available for more precise scanning alignment, and better clearance around neighboring dentition. Additionally, without the need for a fastener, risk of patient aspiration of the fastener is eliminated. Furthermore, the scan body assembly of the present invention is optionally reusable, which offers a cost savings to the practitioner and/or the patient.

While the invention has been described with reference to example embodiments, it will be understood by those skilled in the art that a variety of modifications, additions and deletions are within the scope of the invention, as defined by the following claims.

What is claimed is:

1. A scan body for snap-in retention with a dental implant extending along a first elongate axis, the implant comprising a first engagement section, the scan body comprising:
   an elongate body extending from a first end to a second end and defining a second elongate axis, the elongate body comprising:
   a first end portion comprising a scan feature comprising a plurality of flats configured for recognition by a dental scanner, the plurality of flats comprising an upper flat at the first end of the elongate body and oriented generally perpendicular to the second elongate axis, a lower flat spaced axially toward the second end from the upper flat and oriented generally parallel to the upper flat, and an intermediate flat extending between the upper and lower flats and oriented generally perpendicular to the upper and lower flats;
   an upper section positioned adjacent the first end portion;
   a lower section positioned adjacent the upper section;
   a second engagement section configured for releasable engagement with the first engagement section of the dental implant, the second engagement section positioned adjacent the lower section and comprising at least one engagement element configured to securely engage the first engagement section of the dental implant and retain the scan body in a fixed axial and rotational position relative to the dental implant, and
   a sleeve for fitting on the lower section of the elongate body.

2. The scan body of claim 1, wherein the second engagement section comprises a male hexagonal body and the at least one engagement element comprises a plurality of engagement ribs extending from the male hexagonal body, and wherein the first engagement section comprises a female hexagonal socket configured to receive the male hexagonal body.

3. The scan body of claim 2, wherein the plurality of engagement ribs provide a snap-in frictional fit with the female hexagonal socket.

4. The scan body of claim 2, wherein the male hexagonal body comprises six external surfaces, and further wherein at least one of the plurality of engagement ribs is located on three of the six external contact surfaces.

5. The scan body of claim 4, wherein the three of the six external contact surfaces having at least one engagement rib located thereon are distributed around the male hexagonal body in an alternating sequence.

6. The scan body of claim 5, wherein the three of the six external contact surfaces having at least one engagement rib thereon increase the precision of the scan body and scan feature thereof by axial alignment of the first elongate axis with the second elongate axis.

7. The scan body of claim 1, wherein the sleeve is formed from a titanium alloy or radiopaque material.

8. The scan body of claim 7, wherein the sleeve allows for proper seating verification of the scan body within the implant via x-ray imaging.

9. The scan body of claim 7, wherein the sleeve is color coded by anodizing to match a platform color of the implant.

10. The scan body of claim 1, wherein the elongate body is formed from polyether ether ketone plastic.

11. The scan body of claim 1, wherein the second engagement section of the scan body is configured for both engagement with an implant and with an implant analog.

12. The scan body of claim 1, comprising a channel extending at least partially through the cylindrical portion of the upper section.

13. A snap-in scan body for removable engagement with a dental implant, the implant comprising a receiver, the snap-in scan body comprising:
   an elongate body having a first end portion and a second end portion, the elongate body at least partially comprising a polyether ketone (PEEK) material, the first end portion of the elongate body comprising a scan feature configured for recognition by a dental scanner, the scan feature comprising at least one flat, and the second end portion of the elongate body comprising an engagement section configured for cooperative secure detachable engagement within the receiver of the implant without a fastener, the receiver of the implant comprising a female hexagonal profile, and wherein the engagement section of the scan body comprises a male hexagonal profile configured for secure detachable interengagement within the receiver of the implant; and
   a sleeve for fitting on the lower section of the elongate body, wherein the sleeve allows for proper seating verification of the male hex of the engagement body within the female hex of the receiver of the implant via x-ray.

14. The snap-in scan body of claim 13, wherein the male hexagonal profile of the engagement section comprises six surfaces, and wherein the engagement section further comprises at least one engagement rib provided on at least one of the six surfaces of the male hexagonal profile of the engagement section.

15. The snap-in scan body of claim 14, wherein the at least one engagement rib is provided on three of the six contact surfaces.

16. The snap-in scan body of claim 15, wherein the three of the six contact surfaces having the at least one engagement rib thereon are arranged in an alternating sequence around the hexagonal body.

17. The snap-in scan body of claim 16, wherein the implant defines a first elongate axis and wherein the snap-in scan body defines a second elongate axis, and wherein engagement of the engagement ribs of the male hexagonal profile with the female hexagonal profile of the receiver of the implant maintains a fixed rotational positioning of the scan body relative to the implant, and maintains a precise axial alignment of the first elongate axis with the second elongate axis.

18. The snap-in scan body of claim 13, wherein the sleeve is formed from a titanium alloy or radiopaque material.

19. The snap-in scan body of claim 18, wherein the sleeve is color coded by anodizing to match a platform color of the implant.

20. The snap-in scan body of claim 13, wherein the elongate body further comprises barium sulfate blended with the polyether ether ketone.

21. The snap-in scan body of claim 13, wherein the engagement body is configured for removable engagement with both an implant and with an implant analog.

22. The snap-in scan body of claim 13, wherein the upper section comprises a channel formed therein.

23. A scan body for snap-in retention with a dental implant extending along a first elongate axis, the implant comprising a first engagement section, the scan body comprising:
    an elongate body extending from a first end to a second end and defining a second elongate axis, the elongate body comprising:
        a first end portion comprising a scan feature;
        an upper section positioned adjacent the first end portion and comprising a generally uniform cylindrical portion;
        a lower section positioned adjacent the upper section;
        a second engagement section positioned adjacent the lower section and comprising at least one engagement rib; and
        an end post for axial alignment within an internal threaded portion of the implant; and
    a sleeve for fitting on the lower section of the elongate body.

24. The scan body of claim 23, wherein the sleeve is formed from a titanium alloy or radiopaque material.

25. The scan body of claim 24, wherein the sleeve allows for proper seating verification of the scan body within the implant via x-ray imaging.

26. The scan body of claim 24, wherein the sleeve is color coded by anodizing to match a platform color of the implant.

27. A snap-in scan body for removable engagement with a dental implant, the implant comprising a receiver comprising a female hex, the snap-in scan body comprising:
    an elongate body;
    a first end portion comprising a scan feature comprising at least one flat;
    an upper section adjacent the first end portion;
    a lower section adjacent the upper section and comprising a pair of spaced apart ribs;
    an engagement body adjacent the lower section configured for cooperative detachable engagement within the receiver of the implant, and comprising a male hex configured for engagement with the female hex of the receiver of the implant; and
    a sleeve for fitting on the lower section of the elongate body, wherein the sleeve allows for proper seating verification of the male hex of the engagement body within the female hex of the receiver of the implant via x-ray.

28. The snap-in scan body of claim 27, wherein the sleeve is formed from a titanium alloy or radiopaque material.

29. The snap-in scan body of claim 28, wherein the sleeve is color coded by anodizing to match a platform color of the implant.

30. A scan body for detachable and secure engagement with a cooperative receiver of a dental implant without a separate fastener, the scan body comprising:
    a scan feature comprising a plurality of flats configured for recognition by a dental scanner; and
    an engagement section configured for releasable engagement with the receiver of the dental implant, the engagement section comprising at least one engagement element configured to releasably engage the receiver of the dental implant with a detachable friction fit sufficient to securely engage the scan body on the dental implant for scanning by the dental scanner without the need for a separate fastener and retain the scan body in a fixed axial and rotational position relative to the dental implant during scanning; and
    an engagement shoulder between the scan feature and the engagement section, and a radiopaque sleeve configured for seating between the engagement shoulder and the dental implant for x-ray verification of correct engagement of the scan body with the dental implant,
    wherein the scan body at least partially comprises a polyether ether ketone (PEEK) material.

31. The scan body of claim 30, wherein the plurality of flats of the scan feature comprise an upper flat at a first end of the scan body and oriented generally perpendicular to an elongate axis of the scan body, a lower flat spaced axially from the upper flat and oriented generally parallel to the upper flat, and an intermediate flat extending between the upper and lower flats and oriented generally perpendicular to the upper and lower flats and parallel to the elongate axis of the scan body.

32. The scan body of claim 30, wherein the radiopaque sleeve comprises titanium.

33. The scan body of claim 30, wherein the radiopaque sleeve is color coded by anodizing to match a platform color of the dental implant.

* * * * *